US 6,596,920 B2

(12) United States Patent
Wehner et al.

(10) Patent No.: US 6,596,920 B2
(45) Date of Patent: Jul. 22, 2003

(54) SWIMWEAR WITH FLUID DRAINING MECHANISM

(75) Inventors: Jason K. Wehner, Oak Lawn, IL (US); John E. Kerins, Neenah, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 40 days.

(21) Appl. No.: 09/749,253

(22) Filed: Dec. 27, 2000

(65) Prior Publication Data
US 2002/0082572 A1 Jun. 27, 2002

(51) Int. Cl.[7] .................................................. A61F 13/15
(52) U.S. Cl. ........................ 604/364; 604/381; 604/383
(58) Field of Search ................................. 604/364, 365, 604/367, 375, 386, 387, 389, 378–383; 2/67

(56) References Cited

U.S. PATENT DOCUMENTS

| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,028 A | 11/1970 | Beebe et al. |
| 3,542,615 A | 11/1970 | Dobo et al. |
| 3,692,618 A | 9/1972 | Dorschner et al. |
| 3,802,817 A | 4/1974 | Matsuki et al. |
| 3,804,092 A * | 4/1974 | Tunc ............................ 128/284 |
| 3,849,241 A | 11/1974 | Butin et al. |
| 4,002,171 A * | 1/1977 | Taft ............................. 128/284 |
| 4,011,871 A * | 3/1977 | Taft ............................. 128/284 |
| 4,333,465 A | 6/1982 | Wiegner |
| 4,340,563 A | 7/1982 | Appel et al. |
| 4,372,311 A | 2/1983 | Potts |
| 4,663,220 A | 5/1987 | Wisneski et al. |
| 4,704,116 A | 11/1987 | Enloe |
| 4,790,836 A * | 12/1988 | Brecher ........................ 604/359 |
| 4,940,464 A | 7/1990 | Van Gompel et al. |
| 5,046,272 A | 9/1991 | Vogt et al. |
| 5,104,116 A | 4/1992 | Pohjola |
| 5,110,390 A | 5/1992 | Martini et al. |
| 5,185,009 A * | 2/1993 | Sitnam ......................... 604/364 |
| 5,190,533 A * | 3/1993 | Blackburn ..................... 604/367 |
| 5,224,405 A | 7/1993 | Pohjola |
| 5,226,992 A | 7/1993 | Morman |
| 5,236,428 A | 8/1993 | Zajaczkowski |
| 5,283,090 A | 2/1994 | Umemura |
| 5,981,012 A * | 11/1999 | Pomplun et al. ............ 428/41.8 |
| 5,985,396 A | 11/1999 | Kerins et al. |
| 5,986,004 A * | 11/1999 | Pomplun et al. ............. 525/176 |
| 6,238,266 B1 * | 5/2001 | Vogt ............................. 450/19 |
| 6,294,238 B1 * | 9/2001 | Pomplun et al. ............ 428/41.8 |
| 6,384,297 B1 * | 5/2002 | Colman et al. .............. 604/364 |
| 6,462,251 B1 * | 10/2002 | Cimini et al. ................ 604/358 |

FOREIGN PATENT DOCUMENTS

| DE | 37 03 574 | 8/1988 |
| EP | 461 484 | 12/1991 |
| EP | 0 217 032 | 2/1992 |
| WO | 96/03949 | 2/1996 |

* cited by examiner

Primary Examiner—Weilun Lo
Assistant Examiner—Jamisue A. Webb
(74) Attorney, Agent, or Firm—Pauley Petersen Kinne & Erickson

(57) ABSTRACT

An absorbent swimwear garment having a fluid draining mechanism included in the layers of the garment. The swimwear garment includes a body side liner, an outer cover, and an absorbent assembly between the body side liner and the outer cover. Between the absorbent assembly and the outer cover is a layer of water-dispersible material, such as a film or a nonwoven web, coated on a surface facing the absorbent assembly with a barrier coating. During initial product use, the absorbent swimwear garment is able to contain urine and bowel movements, similar to ordinary diapers and training pants. When the swimwear garment is submersed in swim water, such as pool or lake water, the water-dispersible material becomes soluble and allows swim water, but not bowel movements, to drain out through the outer cover of the garment.

29 Claims, 4 Drawing Sheets

SWIMWEAR WITH FLUID DRAINING MECHANISM

FIELD OF THE INVENTION

This invention is directed to swimpants and swimsuits for pre-toilet trained children. More particularly, the swimwear has a fluid draining mechanism for draining swim water from the garment.

BACKGROUND OF THE INVENTION

Absorbent swim pants and swimsuits for pre-toilet trained children have absorbent cores and moisture barriers to prevent leaks of urine and bowel movements. Because the products are designed for leakage prevention, they retain sizable quantities of swim water, such as pool or lake water, during and after swimming. This retention of water is undesirable because it causes the pants to sag down, is uncomfortable for the wearer, and can soak towels and clothing after swimming.

There is a need or desire for an absorbent swimwear garment that provides uncompromised urine and bowel movement containment before swimming and allows the draining of excess water from the garment during and after swimming.

SUMMARY OF THE INVENTION

The present invention is directed to a pant-like absorbent swimwear garment having a fluid draining mechanism for draining swim water, such as pool or lake water, from the garment. The fluid draining mechanism is dependent on the use of "smart" barrier films, which behave like traditional liquid barriers when insulted from the inside, but quickly disperse when insulted, or exposed to a liquid, from the outside. A swimwear garment having this type of draining mechanism, suitably located in the crotch area of the pant, can exhibit both high capacity before swimming and minimal drooping and water retention during water play.

More particularly, the fluid draining mechanism includes a water-dispersible liquid barrier film that breaks apart and allows pool water to drain from the pant. The water-dispersible liquid barrier film includes a layer of a hydrophobic, barrier resin joined to a water-dispersible substrate. Due to the barrier coating, the dispersion of the liquid barrier film can be delayed until the wearer enters the water, thus providing protection against pre-swim leaks. Bowel movement accidents can still be contained by a body side liner, an absorbent core, and a cloth-like outer cover, even after the liquid barrier film has dispersed. Additionally, the absorbent capacity of the absorbent core can be increased to handle relatively large pre-swim insults since retention of swim water is minimized.

The resulting product is an absorbent swimwear garment that provides uncompromised urine and bowel movement containment before swimming but allows the draining of excess water from the swim pant during and after swimming. Bowel movement containment is not substantially altered before or after swimming.

With the foregoing in mind, it is a feature and advantage of the invention to provide an absorbent swimwear garment with a fluid draining mechanism.

DEFINITIONS

Figure 1:
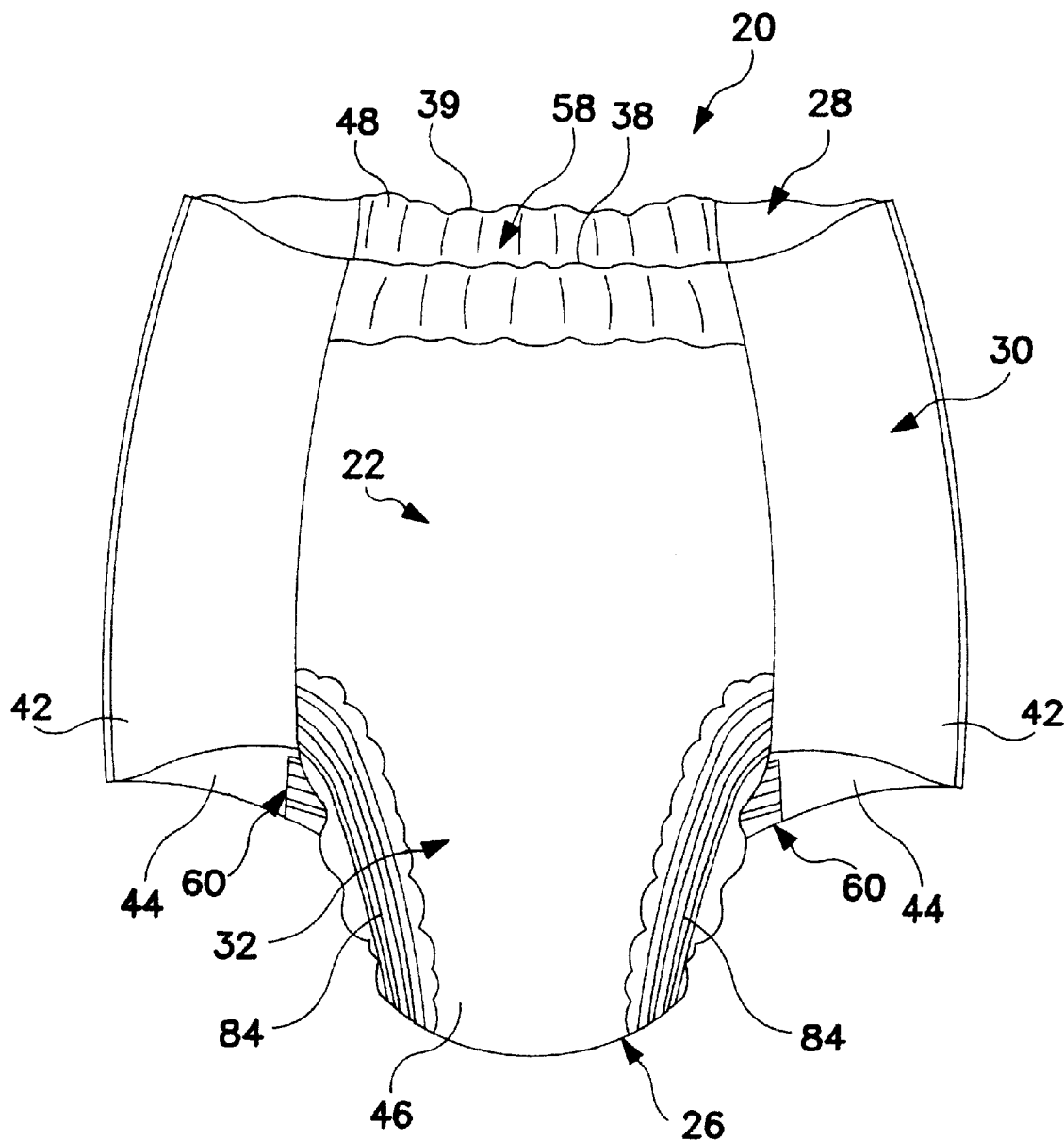
FIG. 1 is a front perspective view of an absorbent swimpant.

Within the context of this specification, each term or phrase below will include the following meaning or meanings.

"Elastic," "elasticized" and "elasticity" mean that property of a material or composite by virtue of which it tends to recover its original size and shape after removal of a force causing a deformation.

"Film" refers to a thermoplastic film made using a film extrusion and/or foaming process, such as a cast film or blown film extrusion process. The term includes apertured films, slit films, and other porous films which constitute vapor transfer films, as well as films which do not transfer liquid, including liquid-impermeable, vapor-permeable films.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Layer" when used in the singular can have the dual meaning of a single element or a plurality of elements.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Liquid-permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

"Meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self-bonding when deposited onto a collecting surface. Meltblown fibers used in the present invention are preferably substantially continuous in length.

"Nonwoven" and "nonwoven web" refer to materials and webs of material which are formed without the aid of a textile weaving or knitting process.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature.

"Water-dispersible" includes water-soluble materials, i.e. materials that dissolve when wet, materials that disintegrate or rupture when wet, materials that otherwise disperse when wet, and materials having a combinations of any of these qualities.

These terms may be defined with additional language in the remaining portions of the specification.

DETAILED DESCRIPTION OF THE PRESENTLY PREFERRED EMBODIMENTS

The present invention is directed to an absorbent swimwear garment having a fluid draining mechanism for draining excess water, such as pool or lake water, from the garment during and after swimming. The principles of the present invention can be incorporated into disposable, pant-like, absorbent swimwear articles, such as swim pants and swimsuits.

Figure 2:
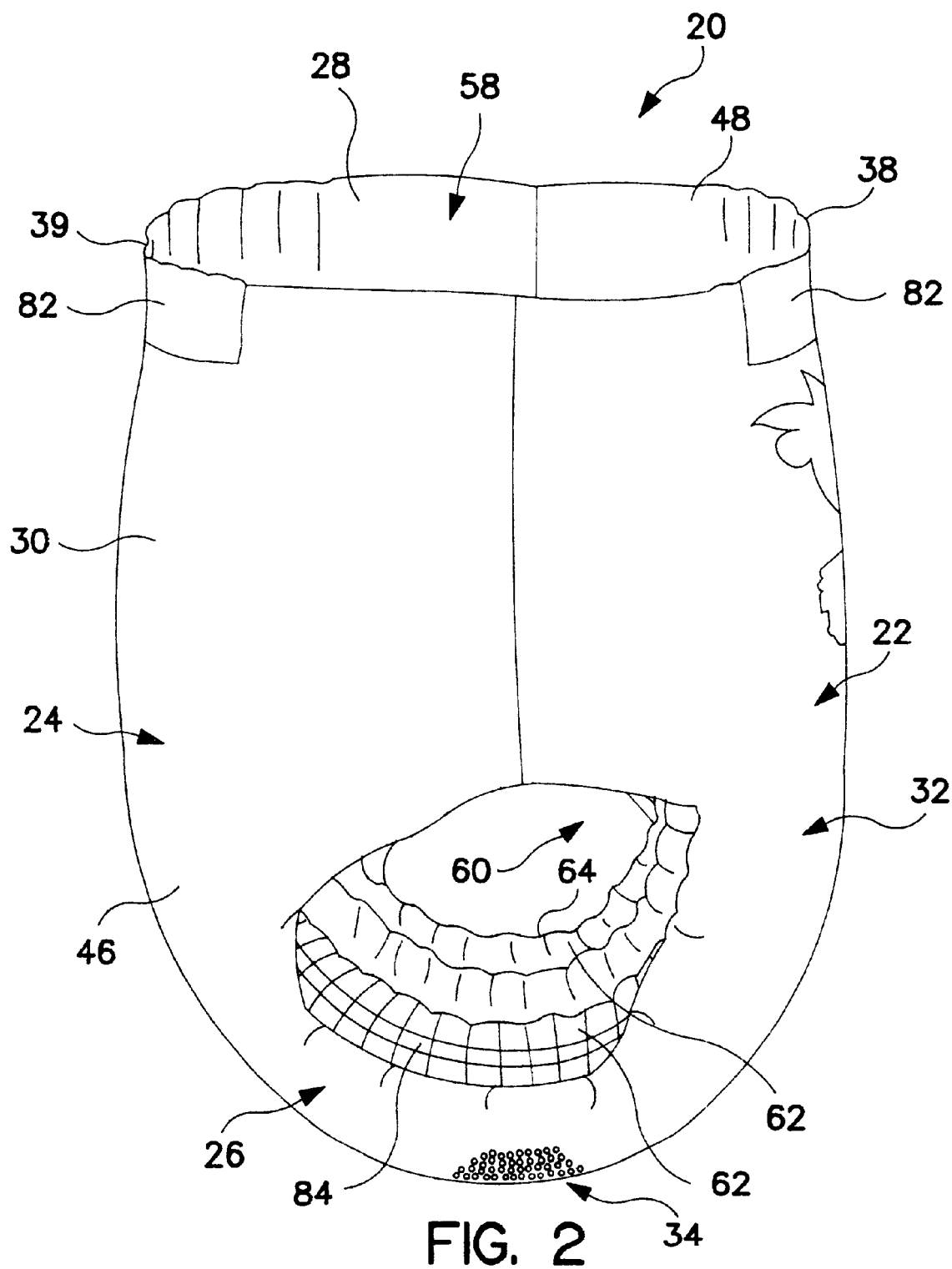
FIG. 2 is a side perspective view of an absorbent swim pant.

Referring to FIGS. 1 and 2, an absorbent swim pant 20 is illustrated. The swim pant 20 includes an absorbent chassis 32. The absorbent chassis 32 defines a front region 22, a back region 24, a crotch region 26 interconnecting the front and back regions, an inner surface 28 which is configured to contact the wearer, and an outer surface 30 opposite the inner surface which is configured to contact a pool or lake environment. Upon contact with a pool or lake environment, a water-dispersible layer within the chassis 32 disperses and allows swim water to exit the swim pant through the outer surface 30, as explained in greater detail below.

Figure 3:
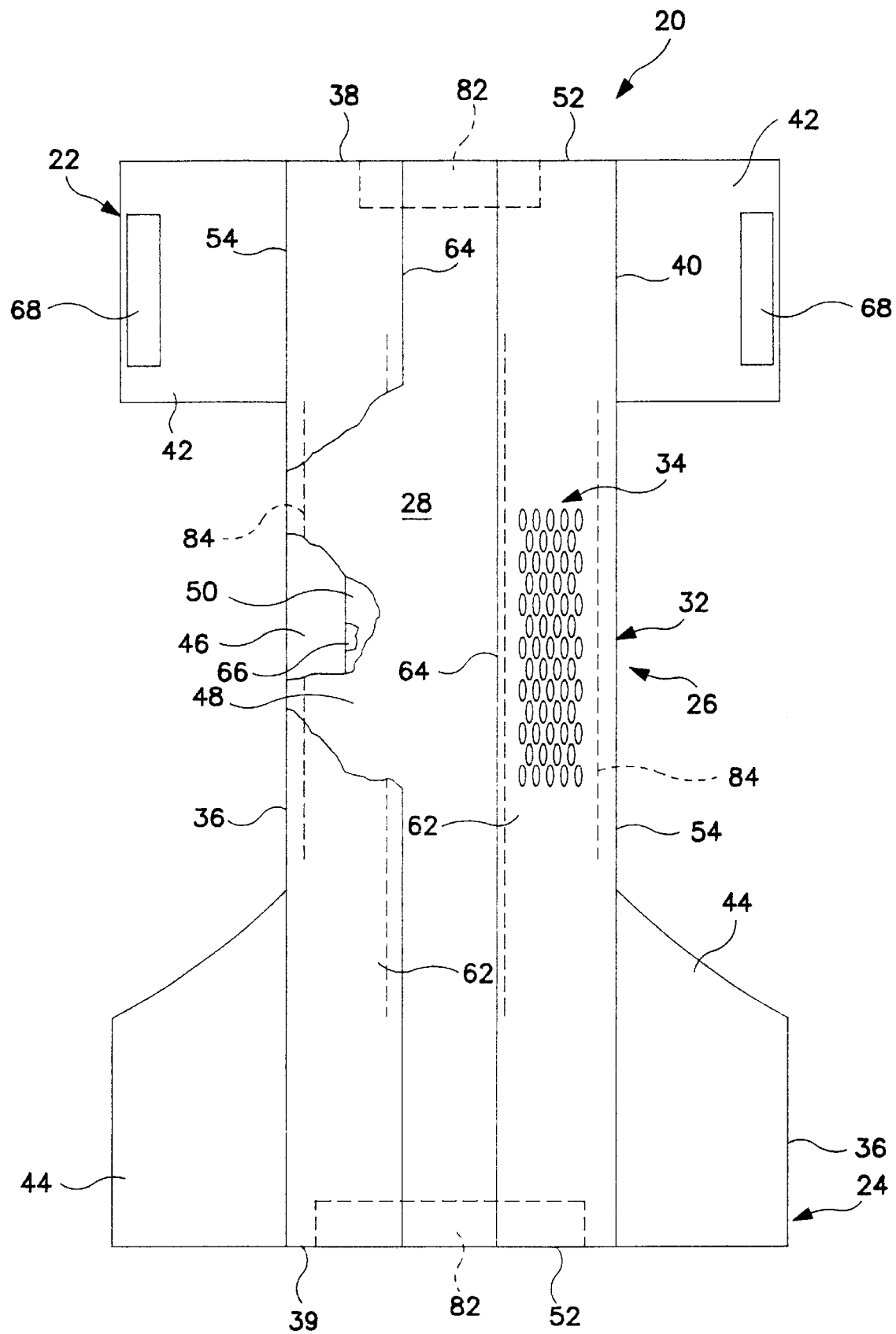
FIG. 3 is a plan view of an absorbent swim pant in a partially disassembled, stretched flat state, and showing the surface of the swim pant that faces the wearer when the swim pant is worn, and with portions cut away to show the underlying features.

Referring to FIG. 3, the swim pant 20 is shown in a partially disassembled, stretched flat state, showing the inner surface 28 which faces the wearer when the garment is worn. As shown, the absorbent chassis 32 also defines a pair of transversely opposed side edges 36 and a pair of longitudinally opposed waist edges, which are designated front waist edge 38 and back waist edge 39. The front region 22 is contiguous with the front waist edge 38, and the back region 24 is contiguous with the back waist edge 39. The chassis 32 also includes a somewhat rectangular composite structure 40, a pair of transversely opposed front side panels 42, and a pair of transversely opposed back side panels 44. The composite structure 40 and side panels 42 and 44 may be integrally formed, as shown in FIG. 2, or may include two or more separate elements, as shown in FIGS. 1 and 3.

The illustrated composite structure 40 includes an outer cover 46, a body side liner 48 which is connected to the outer cover 46 in a superposed relation, and an absorbent assembly 50 which is located between the outer cover 46 and the body side liner 48. Also included in the composite structure 40 is a layer of water-dispersible material 66, suitably located between the outer cover 46 and the absorbent assembly 50. The water-dispersible material 66 is coated on a surface facing the absorbent assembly 50 with a barrier coating 67. Thus, when the swim pant 20 is in use during pre-swim activities, any wetness released within the swim pant 20 is absorbed by the absorbent assembly 50, and any excess liquid that proceeds through the absorbent assembly 50 is contained by the barrier coating 67. The coating inhibits transport of liquid, providing a barrier between the fluid and the water-dispersible substrate. However, when the swim pant 20 is submersed in swim water, such as pool water or lake water, the swim water approaches the water-dispersible material through the outer cover and causes the water-dispersible material to dissolve, disintegrate, or otherwise disperse. The barrier coating 67 has little mechanical integrity in the absence of the substrate, and so readily breaks open, thereby allowing any excess liquids in the swim pant to drain out of the swim pant 20. The rectangular composite structure 40 has opposite linear end edges 52 that form portions of the front and back waist edges 38 and 39, and opposite linear, or curvilinear, side edges 54 that form portions of the side edges 36 of the absorbent chassis 32.

As shown in the swim pants 20 in FIGS. 1 and 2, the front and back regions 22 and 24 together define a three-dimensional pant configuration having a waist opening 58 and a pair of leg openings 60. The waist edges 38 and 39 of the absorbent chassis 32 are configured to encircle the waist of the wearer when worn and provide the waist opening 58 which defines a waist perimeter dimension Portions of the transversely opposed side edges 36 (FIG. 3) in the crotch region 26 generally define the leg openings 60. The front region 22 includes the portion of the swim pant 20 which, when worn, is positioned on the front of the wearer while the back region 24 includes the portion of the swim pant 20 which, when worn, is positioned on the back of the wearer. The crotch region 26 of the swim pant 20 includes the portion of the swim pant 20 which, when worn, is positioned between the legs of the wearer and covers the lower torso of the wearer.

The absorbent chassis 32 is configured to contain and/or absorb any body exudates discharged from the wearer, particularly prior to swimming. The containment of solid body exudates is not compromised by exposure of the swim pant to swim water. For example, the absorbent chassis 32 can include a pair of elasticized containment flaps 62 (shown in FIGS. 2 and 3) which are configured to provide a barrier to the transverse flow of body exudates. The elasticized containment flaps 62 define an unattached edge 64 which assumes an upright, generally perpendicular configuration in at least the crotch region 26 of the swim pant 20 to form a seal against the wearer's body. Suitable constructions and arrangements for the containment flaps 62 are generally well known to those skilled in the art and are described in U.S. Pat. No. 4,704,116 issued Nov. 3, 1987 to Enloe, which is incorporated herein by reference.

Absorbent swimwear is designed for leakage prevention. Thus, when a wearer wears absorbent swimwear into a pool or lake, the swimwear has a tendency to fill up with water, particularly in the crotch region 26. Therefore, the water-dispersible material is designed to disperse when the swim pant 20 is submerged in swim water to allow the swim water to drain out of the swim pant 20. As used herein, the term "water-dispersible material" includes water-soluble, water-softenable or water-weakened material, such as a material that becomes a gel in water, and that can be easily dispersed by water pressure inside the swim pant 20 or by the mechanical stresses associated with movement of the swim pant. The outer cover of the swim pant can either be made of a liquid-permeable material, or can include a liquid-impermeable material having apertures 34 in the liquid-impermeable material covered by the water-dispersible material, as shown in FIGS. 2 and 3, such that liquid could drain through the apertures 34 once the water-dispersible material is broken up or disintegrated. In the embodiment wherein the outer cover includes a liquid-impermeable material, the apertures 34 can be strategically located in the crotch region (FIG. 2) and/or in the containment flaps (FIG. 3) for targeted draining in the areas where drainage is most necessary. The apertures 34 can include holes, cuts, slits or gaps in seams in the outer surface 30 of the crotch region 26, as shown in FIG. 2, or in the containment flaps 62, as shown in FIG. 3. When the barrier coating 67 is in place on the water-dispersible material 66 and the surface of the water-dispersible material 66 opposite the barrier coating 67 is not exposed to swim water, the swim pant 20 works similar to regular diapers and training pants, absorbing any urine and containing any bowel movements excreted by the wearer.

When the swim pant 20 is submerged in water, such as when a wearer is swimming or wading in a pool or a lake, the water-dispersible material 66 breaks down (disintegrates), dissolves, and/or otherwise disperses, allowing excess water and urine not held in the absorbent assembly 50 to flow out the swim pant 20 through the outer cover. The barrier coating 67 has little mechanical integrity on its own, and thus breaks up and opens to the flow of excess water when the water dispersible material 66 begins to disperse. Bowel movement material is kept inside the swim pant 20 regardless of whether the water-dispersible material disperses or not, because the body side liner material 48 is constructed as in a normal absorbent garment, such as a diaper or training pant, to keep bowel movements contained.

Figure 4:
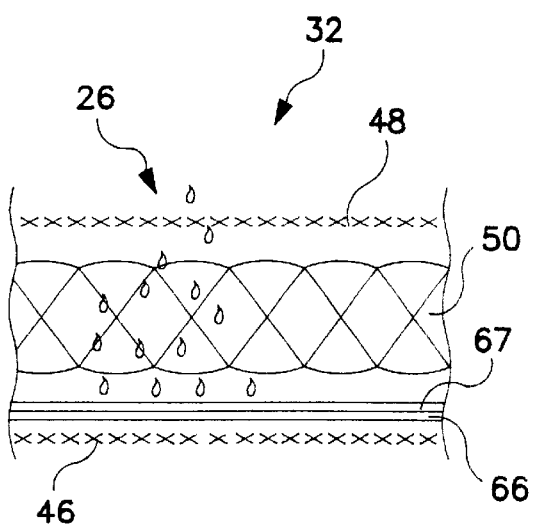
FIG. 4 is a cross-sectional view of the composite chassis of the swim pant before swimming.
Figure 5:
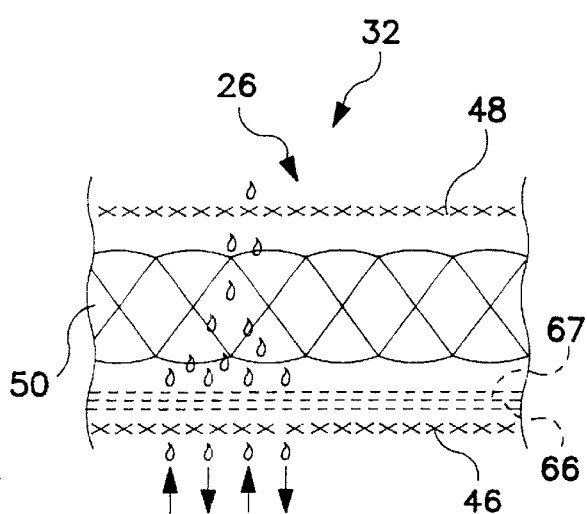
FIG. 5 is a cross-sectional view of the composite chassis of the swim pant during or after swimming, when the draining mechanism is activated.

FIG. 4 shows a cross-sectional view of the crotch region 26 of the composite chassis 32 of the swim pant 20 before swimming. The body side liner 48 is situated adjacent the wearer's skin when the swim pant 20 is worn. Fluids, i.e., urine, can flow through the body side liner 48 and are then absorbed into the absorbent assembly 50. The outer cover 46 is substantially liquid permeable, or can be substantially liquid impermeable with apertures as mentioned, and has a cloth-like texture. The water-dispersible layer 66 is between the absorbent assembly 50 and the outer cover 46, with the barrier coating 67 on a surface of the water-dispersible layer 66 facing the absorbent assembly 50. The water-dispersible layer 66 can be in the form of a film or nonwoven web or other suitable material. FIG. 5 shows a cross-sectional view of the crotch region 26 of the composite chassis 32 of the swim pant 20 during or after swimming, when the water-dispersible layer 66 has dispersed, thus allowing the thin, weak barrier coating 67 to disperse as well. The body side liner 48, absorbent assembly 50, water-dispersible layer 66, and outer cover 46 can be joined together by any suitable means, such as adhesives, as is well known in the art.

The water-dispersible material 66 is generally 0.25 mil to about 2.5 mils thick, suitably 0.35 mil to 2.2 mils thick, more suitably 0.45 mil to 2.0 mils thick. The barrier coating 67 is generally 0.05 mil to about 1.0 mil thick, suitably 0.08 mil to about 0.9 mil thick, more suitably 0.1 mil to 0.8 mil thick. When the swim pant 20 is worn while swimming, the water dilutes any urine that may be present and solubilizes the water-dispersible layer 66, thereby allowing the excess water within the swim pant 20 to drain out while still maintaining any bowel movements within the swim pant 20.

One example of a water-dispersible material suitable for the water-dispersible layer 66 is a water-dispersible polyethylene-oxide resin. The polyethylene-oxide, or other water-dispersible material, can be coated on one side with a thin, weak layer of barrier material 67, such as an amorphous polyalphaolefin or a poly-caprolactone. The barrier material 67 can be applied to the water-dispersible material 66 either as a continuous coating or a closely-spaced discontinuous coating, thereby providing enough coverage to repel liquids while maintaining a weak enough structure to be dispersible upon contact with a considerable amount of swim water.

In the case of a discontinuous coating, the spaces between the coating spots must be close enough that water is precluded by capillary forces from flowing between the spots to the underlying substrate. Desirably, the barrier coating is a polyalphaolefin having a melt viscosity of about 400 to about 10,000 cps at 190 degrees Celsius. Suitable polymers include, but are not limited to, low molecular weight, amorphous ethylene-propylene copolymers. Particularly suitable polymers are manufactured by the U.S. Rexene Company under the tradename REXTAC®.

Water-dispersible films coated with a barrier layer are described in U.S. Pat. Nos. 4,372,311; 5,283,090; and 5,110,390, all of which are incorporated herein by reference. Other examples of water-dispersible materials include, without limitation, ethylene oxide/propylene oxide copolymers, polymethacrylic acid, polymethacrylic acid copolymers, polyvinyl alcohol, poly(2-ethyl oxazoline), polyvinyl methyl ether, polyvinyl pyrrolidone/vinyl acetate copolymers, methyl cellulose, ethyl cellulose, hydroxypropyl cellulose, hydroxypropyl methyl cellulose, ethyl hydroxyethyl cellulose, methyl ether starch, poly (n-isopropyl acrylamide), poly N-vinyl caprolactam, polyvinyl methyl oxazolidone, poly (2-isopropyl-2-oxazoline), poly (2,4-dimethyl-6-triazinyl ethylene), and combinations thereof. Examples of barrier coating materials include, without limitation, polyethylene, ethylene/vinyl acetate copolymers, polypropylene, polyesters and other water-insoluble thermoplastic resins, and combinations thereof. The barrier coating 67 must be thin or weak enough that it ruptures or otherwise disperses when the water-dispersible layer 66 disperses.

The absorbent assembly 50, positioned between the water-dispersible material 66 and the body side liner 48, can be any structure which is generally compressible, conformable, non-irritating to the child's skin, and capable of absorbing and retaining liquids and certain body wastes. The absorbent assembly 50 can be manufactured in a wide variety of sizes and shapes, and from a wide variety of liquid absorbent materials commonly used in the art. For example, the absorbent assembly 50 can suitably include a matrix of hydrophilic fibers, such as a web of cellulosic fluff, mixed with particles of a high-absorbency material commonly known as superabsorbent material. In a particular embodiment, the absorbent assembly 50 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be non-uniformily mixed. The fluff and superabsorbent particles can also be selectively placed into desired zones of the absorbent assembly 50 to better contain and absorb body exudates. The concentration of the superabsorbent particles can also vary through the thickness of the absorbent assembly 50. Alternatively, the absorbent assembly 50 can include a laminate of fibrous webs and superabsorbent material or other suitable means of maintaining a superabsorbent material in a localized area. Another type of absorbent material suitable for the absorbent assembly 50 is co-form, which is a blend of staple length and melt-blown fibers. The weight ratio of staple fibers to melt-blown fibers may range between 30 (staple)/70 (melt-blown) and 90 (staple)/10 (melt-blown). Wood pulp fibers are preferred for the staple fibers and polypropylene is preferred for the melt-blown fibers. Superabsorbent materials may be added to the co-form to increase capacity.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 50 is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 50 in an amount of from about 0 to about 90 weight percent based on total weight of the absorbent assembly 50. The absorbent assembly 50 suitably has a density within the range of about 0.10 to about 0.35 grams per cubic centimeter. The absorbent assembly 50 may or may not be wrapped or encompassed by a suitable tissue wrap that maintains the integrity and/or shape of the absorbent assembly 50.

The outer cover 46 suitably includes a material that is either substantially liquid permeable or substantially liquid impermeable with apertures 34, and can be elastic, stretchable or nonstretchable. The outer cover 46 can be a single layer of material, but desirably includes a multi-layered laminate structure. For instance, the outer cover 46 can include a single liquid permeable layer, or a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable layer can be any suitable material and desirably one that provides a generally cloth-like texture. One example of such a material is a 20 gsm (grams per square meter) spunbond polypropylene nonwoven web. The liquid permeable layer may also be made of those materials of which liquid permeable body side liner 48 is made. It is desired that the liquid permeable layer provides a relatively cloth-like texture to the wearer.

The liquid impermeable inner layer of the outer cover 46 can be both liquid and vapor impermeable, or can be liquid impermeable and vapor permeable. The inner layer, if present, is desirably manufactured from a thin plastic film, although other flexible liquid impermeable materials may also be used. The inner layer prevents waste material from wetting articles, such as car seats and clothing, as well as the wearer and caregiver. A suitable liquid impermeable film for use as a liquid impermeable inner layer, or a single layer liquid impermeable outer cover 46 with apertures 34, is a 0.02 millimeter polyethylene film commercially available from Huntsman Packaging of Newport News, Va., U.S.A. If the outer cover 46 is a single layer of liquid impermeable material, it can be embossed and/or matte finished to provide a more cloth-like appearance. As earlier mentioned, the liquid impermeable material can permit vapors to escape from the interior of the disposable absorbent article, while still preventing liquids from passing through the outer cover 46. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

The liquid permeable body side liner 48 is illustrated as overlying the outer cover 46 and absorbent assembly 50 (FIG. 3), and may but need not have the same dimensions as the outer cover 46. The body side liner 48 is desirably compliant, soft feeling, and non-irritating to the child's skin. Further, the body side liner 48 can be less hydrophilic than the absorbent assembly 50, to present a relatively dry surface to the wearer and permit liquid to readily penetrate through its thickness.

The body side liner 48 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body side liner 48. For example, the body side liner 48 can be composed of a meltblown or spunbonded web of polyolefin fibers. The body side liner 48 can also be a bonded-carded web composed of natural and/or synthetic fibers. The body side liner 48 can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. The surfactant can be applied by any conventional means, such as spraying, printing, brush coating or the like. The surfactant can be applied to the entire body side liner 48 or can be selectively applied to particular sections of the body side liner 48, such as the medial section along the longitudinal centerline.

A suitable liquid permeable body side liner 48 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multilobe, side-by-side, end-to-end, or the like. While the outer cover 46 and body side liner 48 can include elastomeric materials, it can be desirable in some embodiments for the composite structure to be generally inelastic, where the outer cover 46, the body side liner 48 and the absorbent assembly 50 include materials that are generally not elastomeric.

As noted previously, the illustrated training pant 20 can have front and back side panels 42 and 44 disposed on each side of the absorbent chassis 32 (FIGS. 1 and 3). These transversely opposed front side panels 42 and transversely opposed back side panels 44 can be permanently bonded to the composite structure 40 of the absorbent chassis 32 and can be permanently bonded to one another along corresponding sides. Alternatively, the front and back side panels 42, 44 can be releasably attached to one another by a fastening system 68. The side panels 42 and 44 may be attached to the composite structure 40 and/or to one another using attachment means known to those skilled in the art such as adhesive, thermal or ultrasonic bonding. The side panels 42 and 44 can also be formed as a portion of a component of the composite structure 40, such as the outer cover 46 or the body side liner 48.

Suitable elastic materials, as well as one described process of incorporating elastic side panels into an absorbent garment, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may include other woven or nonwoven materials, such as those described above as being suitable for the outer cover 46 or body side liner 48, or stretchable but inelastic materials.

To further enhance containment and/or absorption of body exudates, the swim pant 20 can include waist elastic members 82 and/or leg elastic members 84, as are known to those skilled in the art (FIGS. 1–3). The waist elastic members 82 can be operatively joined to the outer cover 46 and/or to the body side liner 48, and can extend over part or all of the waist edges 38, 39. The leg elastic members 84 are desirably operatively joined to the outer cover 46 and/or to the body side liner 48 longitudinally along the opposite side edges 36 and positioned in the crotch region 26 of the swim pant 20.

The waist elastic members 82 and the leg elastic members 84 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the waist elastic members 82 and/or the leg elastic members 84 include a plurality of dry-spun coalesced multifilament spandex elastomeric threads sold under the trade name LYCRA® and available from E.I. du Pont de Nemours and Company, Wilmington, Del., U.S.A. In another particular embodiment, for example, the waist elastic members 82 and/or the leg elastic members 84 include Findley HX 2695-01 adhesive laminated to two facings of 0.6 osy (ounces per square yard) bicomponent polypropylene/polyethylene spunbond. Alternatively, several strands of 310 decitex LYCRA® may be also laminated at 250% elongation between the spunbond facings in addition to the Findley adhesive.

As described herein, the various components of the swim pant 20 can be integrally assembled together employing various types of suitable attachment means, such as adhesive, sonic and thermal bonds or combinations thereof. The resulting product is an absorbent swim pant 20 that provides uncompromised urine and bowel movement containment before swimming, but allows draining of excess water from the swim pant 20 during and after swimming without substantially altering bowel movement containment.

EXAMPLES

In a first example, polyethylene oxide resin blended with calcium carbonate and titanium dioxide was cast into a 1.2 mil film and slot coated with a 0.6 mil layer of hydrophobic amorphous polyalphaolefin, sold by U.S. Rexene Company under the trade name REXTAC® RTE32, for an overall thickness of 1.8 mil. The bilayer structure was tested by holding the film in a sink under lukewarm water running from the tap. The bilayer structure effectively broke and dispersed in less than three minutes when wet from the polyethylene oxide side, yet kept the polyethylene oxide dry when placed so the water was running off the amorphous polyalphaolefin side.

In a second example, a bilayer structure of a water-dispersible polyethylene oxide substrate layer coated with a barrier polycaprolactone layer was coextruded, such that 90% of the bilayer structure by weight was the polyethylene oxide and 10% by weight was the poly-caprolactone. The overall thickness of the bilayer structure was 0.54 mil. The same procedure described above was used to test this bilayer structure. The bilayer structure was observed to disperse when wet from the polyethylene oxide side, however a considerable amount of exposure time to the running water, approximately five minutes, and increased flow and pressure from the tap, were required due to the higher strength of the poly-caprolactone. The structure did not disperse when only the poly-caprolactone side was exposed to liquid.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. An absorbent garment comprising:
    a chassis including an outer cover and a body side liner, and defining a waist opening and first and second leg openings, the outer cover having a plurality of apertures in a crotch region of the chassis; and
    a water-dispersible film situated between the outer cover and the body side liner, including a barrier coating on a surface of the water-dispersible film facing the body side liner.

2. The absorbent garment of claim 1, further comprising an absorbent assembly situated between the body side liner and the water-dispersible film.

3. The absorbent garment of claim 1, wherein the outer cover comprises a liquid permeable nonwoven web.

4. The absorbent garment of claim 1, wherein the outer cover comprises a liquid impermeable layer.

5. The absorbent garment of claim 1, wherein the water-dispersible film comprises polyethylene oxide.

6. The absorbent garment of claim 1, wherein the barrier coating comprises a hydrophobic, low molecular weight, amorphous polyalphaolefin layer.

7. The absorbent garment of claim 6, wherein the hydrophobic, low molecular weight, amorphous polyalphaolefin layer comprises a melt viscosity in a range between about 400 and about 10,000 cps at 190 degrees Celsius.

8. The absorbent garment of claim 1, wherein the barrier coating comprises poly-caprolactone.

9. The absorbent garment of claim 1, wherein the barrier coating is applied in a continuous layer over the water-dispersible film.

10. The absorbent garment of claim 1, wherein the barrier coating is applied in a discontinuous layer over the water-dispersible film.

11. The absorbent garment of claim 1, wherein the barrier coating is slot coated onto the water-dispersible film.

12. The absorbent garment of claim 1, wherein the barrier coating and the water-dispersible film are co-extruded.

13. Swimwear comprising the absorbent garment of claim 1.

14. An absorbent garment comprising:
    a chassis including an outer cover and a body side liner, and defining a waist opening and first and second leg openings, the outer cover having a plurality of apertures in a crotch region of the chassis; and
    a water-dispersible nonwoven web situated between the outer cover and the body side liner, including a barrier coating on a surface of the water-dispersible nonwoven web facing the body side liner.

15. The absorbent garment of claim 14, further comprising an absorbent assembly situated between the body side liner and the water-dispersible nonwoven web.

16. The absorbent garment of claim 14, wherein the outer cover comprises a liquid permeable nonwoven web.

17. The absorbent garment of claim 14, wherein the outer cover comprises a liquid impermeable layer.

18. The absorbent garment of claim 14, wherein the barrier coating is applied in a continuous layer over the water-dispersible nonwoven web.

19. The absorbent garment of claim 14, wherein the barrier coating is applied in a discontinuous layer over the water-dispersible nonwoven web.

20. Swimwear comprising the absorbent garment of claim 14.

21. An absorbent swimwear garment comprising:
    a chassis defining a waist opening and first and second leg openings, the chassis including a body side liner, an outer cover having a plurality of apertures in a crotch region of the chassis, and an absorbent assembly between the body side liner and the outer cover; and
    a layer of water-dispersible material situated between the outer cover and the absorbent assembly, including a barrier coating on a surface of the water-dispersible material facing the absorbent assembly.

22. The absorbent garment of claim 21, wherein the outer cover comprises a liquid permeable nonwoven web.

23. The absorbent garment of claim 21, wherein the outer cover comprises a liquid impermeable layer.

24. The absorbent garment of claim 21, wherein the barrier coating is applied in a continuous layer over the water-dispersible material.

25. The absorbent garment of claim 21, wherein the barrier coating is applied in a discontinuous layer over the water-dispersible material.

26. The absorbent garment of claim 21, wherein the water-dispersible material is between about 0.25 and 2.5 mils thick.

27. The absorbent garment of claim 21, wherein the water-dispersible material is between about 0.35 and 2.2 mils thick.

28. The absorbent garment of claim 21, wherein the water-dispersible material is between about 0.45 and 2.0 mils thick.

29. Swimwear comprising the absorbent garment of claim 21.

* * * * *